United States Patent [19]

Botzolakis et al.

[11] Patent Number: 4,910,023

[45] Date of Patent: Mar. 20, 1990

[54] DRUG IN COMBINATION WITH FLAVOR MASKING AGENT AND METHOD FOR MAKING SAME

[75] Inventors: John E. Botzolakis, Randolph; Michael R. Harris, Hackettstown; Russell U. Nesbitt, Somerville, all of N.J.

[73] Assignee: Warner-Lambert Company, Morris Plains, N.J.

[21] Appl. No.: 204,437

[22] Filed: Jun. 9, 1988

[51] Int. Cl.$^4$ .............................................. B61K 9/26
[52] U.S. Cl. ..................................... 424/470; 424/464; 424/465
[58] Field of Search ...................... 424/470, 464, 465

[56] References Cited

U.S. PATENT DOCUMENTS

| | | | |
|---|---|---|---|
| 4,327,076 | 4/1982 | Puglia et al. | 424/441 |
| 4,327,077 | 4/1982 | Puglia et al. | 424/441 |

*Primary Examiner*—Ellis P. Robinson
*Assistant Examiner*—Leon R. Horne
*Attorney, Agent, or Firm*—Daniel A. Scola, Jr.; Howard Olevsky

[57] ABSTRACT

According to this invention various hygroscopic malflavored drugs can be proceeded by a unique wet granulation process wherein a slurry of the drug in water is dried in combination with colloidal silicon dioxide and, in a particularly preferred embodiment microcrystalline cellulose with the colloidal silicon dioxide absorbing onto the drug particles.

The result is a protective coating of silicon dioxide which masks unpleasant taste and odor and also reduces the adhesive of the granulation onto the punch faces used in the manufacture of the granules. By adsorbing silicon dioxide on the particulate surface of the malflavored hygroscopic drug, the drug becomes not only easier to handle but the unpleasant tastes and/or odors are masked making the fiinal product more susceptible to proper patient compliance.

11 Claims, No Drawings

DRUG IN COMBINATION WITH FLAVOR MASKING AGENT AND METHOD FOR MAKING SAME

BACKGROUND OF THE INVENTION

Drugs are most commonly administered orally and as such must be placed in a suitable form for oral ingestion. Not only must the drug be adapted to be delivered at desirable dosage levels but, at times, depending upon the nature of the drug, must be protected from rapid moisture absorption.

Certain hygroscopic drugs have distinctly unpleasant tastes and odors. In addition hygroscopic and waxy drugs present processing problems during tabletting and encapsulation. Examples of drugs which possess one or more of these properties are oxtriphylline, procainamide HCl, gemfibrozil, disopyramide phosphate, fenoprofen calcium, atenolol, piracetam, carbamazepine, tetracycline HCl, oxytetracycline HCl, rifamprin, lincomycin HCl, clindamycin HCl, cefaclor, cefadroxil, cephrabine, thiamine HCl, ascorbic acid, acetysalicylic acid, methocarbamol, methyldopa, sulindac, desipramine HCl, ranitine HCl, ethionamide, divalproex sodium, meprobamate, captopril, and aminophylline. These drugs as well as other hygroscopic unpleasant tasting drugs are known for purposes of this specification as malflavored drugs and, because of their off flavors and difficult handling, provide problems both for the drug manufacturer as well as in the area of patient compliance in taking proper amounts.

Silicon dioxide is an ingredient commonly used in the tablet art as an aid to tablet processing. Low levels of silicon dioxide usually below 2% are generally employed. European Patent Application 108,218 by James Michael Dunn et al describes the formation of constant release rate tablets of water soluble drugs employing from 0.5 to 3 rate percent of fumed silicon dioxide as a lubricant.

U.S. Pat. No. 4,536,511 issued to Wolfgang Fisher et al, discloses a drug specific combination including levels of silica and cellulose below 1% evidently to aid binding and flow characteristics in a wet granulation system for the drug muzolimine.

U.S. Pat. No. 4,526,777 issued to Cheryl D. Blume et al discloses the combination of two dry granulations including microcrystalline cellulose as a binding and disintergrant with syloid as a flow enhancer again in precedingly low levels.

Patents issued to James M. Dunn, namely U.S. Nos. 4,461,759; 4,522,804; 4,521,402; and 4,521,401 disclose 0.4 to 3.09% silicon dioxide in combination with hydrogenated vegetable oil and an acrylic acid polymer.

U.S. Pat. No. 4,609,675 issued to Robert M. Franz discloses using silicon dioxide at a 1% level for dry granulation of ibuprofen.

U.S. Pat. No. 4,478,819 issued to Hercelin, teaches silicon dioxide used in forming extruded granules. U.S. Pat. No. 4,442,086 issued to James M. Quinlan discloses the use of silica as a glidant at levels not greater than 0.05%.

U.S. Pat. No. 4,415,547 teaches the use of silica dioxide as a dusting powder for pellets which are subsequently compressed into tablets.

U.S. Pat. No. 3,592,927 issued to Maximillan Koffier discloses a calcium pantothenate composition which is produced in dry free flowing form by the inclusion of silicon dioxide during its manufacturer at a level below 5%.

In addition, European Patent Application 167,191 discloses the inclusion of silicon dioxide as an aid to direct compression of tablets. European Patent Application 136,100 discloses the combination of sucralfate with microcrystalline cellulose and colloidal silicon dioxide as a suspending agent at extremely low levels.

SUMMARY OF THE INVENTION

According to this invention various unpleasant flavored drugs can be processed by a unique wet granulation process wherein a slurry of the drug in water is dried in combination with colloidal silicon dioxide and, in a particularly preferred embodiment microcrystalline cellulose is used with the colloidal silicon dioxide adsorbing onto the drug particles.

By unpleasant flavored drugs, for purposes of this invention, the term is defined as drugs which are unpleasant tasting and/or smelling and/or are hygroscopic and/or tacky.

The result is a protective coating of silicon dioxide which masks unpleasant taste and odor, decreases moisture absorption, and also reduces the adhesiveness of the granulation onto the punch faces used in the manufacture of the granules. By adsorbing silicon dioxide on the particulate surface of the malflavored hygroscopic drug, the drug becomes not only easier to handle but the unpleasant tastes and/or odors are masked making the final product more susceptible to proper patient compliance.

DETAILED DESCRIPTION OF THE INVENTION

Levels of silicon dioxide generally greater than 3% by weight of the combination of the drug and the other solid components are necessary to provide a noticeable masked effect and in fact levels of between 4 and 15% of silicon dioxide are particularly preferred although, with certain particularly unpleasant drugs levels of silicon dioxide approaching 30% can be utilized within the teachings of this invention.

The drug used in the combination is usually present at a level of 30 to 70% by weight with other commonly used granulating and tabletting aids being added as necessary or desired as within the skill of the art to provide a total dry weight combination of 100%.

Particularly preferred is the addition of a drying adjunct with microcrystalline cellulose being especially preferred at levels up to about 45% by weight of the combination. Microcrystalline cellulose also serves as a filler/binder which helps form particularly suitable granules and aids in the compression of the granules during tabletting.

As mentioned above, this invention involves a unique wet granulation process wherein colloidal silicon dioxide and preferably other excipients, especially microcrystalline cellulose are adsorbed onto particles of a particular hygroscopic malflavored drug. Once the granulation process is completed the mixture is dried in an oven, milled and tabletted to an appropriate sized tablet. Lubricants and disintegrants may be added to the formulation prior to tabletting as well as suitable coloring agents as is well known in the art. Tablets with excellent compressibility and over 20 kg hardness may be achieved at relatively low tabletting forces. The same process is useful for preparing granules to be placed in hard gelatin capsules.

In addition, film coating can be used to provide an additional moisture barrier.

Drugs which particularly benefit from the process of this invention are 3-phenoxypyridine monosulfate pramiracetam, and gemfibrozil. When these drugs are used in combination with from 3 to 20% and particularly 5 to 20% of silicon dioxide the difficulties inherent in their manufacture are substantially diminished and the malflavor of these drugs is also minimized. (Pramiracetam is (N-[2-]Bis(1-methylethyl)amino]ethyl]-2-oxo-1-pyrolidine acetamide, sulfate (1:1)).

Examples of the process of this invention follow with two specific drugs used. It is to be understood that the examples are merely illustrative of malflavor drugs. The ingredients used in the first example are set forth in the table below.

EXAMPLE 1

TABLE I

| Ingredients TABLET CORE | Per 1000 |
| --- | --- |
| 3 phenoxypyridine monosulfate | 786.450 g |
| Colloidal Silicon Dioxide NF | 2.359 g |
| Water, Purified | 120.000 ml |
| Sodium Lauryl Sulfate NF | 2.280 g |
| Crospovidone NF | 22.800 g |
| Colloidal Silicon Dioxide NF | 177.911 g |
| Microcrystalline Cellulose NF Powder | 91.200 g |
| Crospovidone NF | 34.000 g |
| Calcium Stearate NF, Powder | 11.400 g |
| Talc USP | 11.400 g |
| Water, Purified | q.s. |
| | 1140.00 g |

A sample was prepared as indicated by first milling the drug with colloidal silicon dioxide through a 1B screen utilizing a hammer mill. Separately, sodium lauryl sulfate is added to water in a planetary mixer and then the aqueous mixture is mixed with the combination of silicon dioxide and 3 phenoxypyridine monosulfate. Crospovidone is then added to aid in disintegration.

Colloidal silicon dioxide is then added and mixed for about 5 minutes followed by the addition of microcrystalline cellulose. The granulation is then dried in an oven at 50° C. to a moisture content of less than 0.5% and further processed by milling through a 1B screen and then combined with calcium stearate, crospovidone and talc. Tablets are formed by compressing 1140 mg of the mixture to a hardness generally between 18 and 20 Kgm using an ellipital punch.

The tablet is then film coated with a mixture of about 4% coat containing hydroxypropylmethylcellulose.

EXAMPLE 2

EXAMPLE 2

| TABLET CORE | |
| --- | --- |
| Pramiracetam (salt equivalent) | 544.200 g |
| Water, Purified | 95.000 ml |

EXAMPLE 2-continued

| TABLET CORE | |
| --- | --- |
| Colloidal Silicon Dioxide NF | 50.000 g |
| Microcrystalline Celluoose NF | 328.880 g |
| Crospovidone NF | 61.200 g |
| Calcium Stearate NF, Power | 25.500 g |
| Talc USP | 10.200 g |
| | 1020.000 g |

The drug in accordance with this invention is made as follows: first the pramiracetam was dissolved in water in a planetary type mixer and then colloidal silicon was added and mixed for about 5 minutes to partially dry the slurry. Subsequently microcrystalline cellulose was added and mixing continued for approximately 5 minutes. The granulation was then dried at 35° C. for 6 hours and dried subsequently at 50° C. to a moisture content of less than 1%. The granulation was then milled through a 1B screen with knives forward at medium speed and calcium stearate was then added to the screen with a subsequent addition of crospovidone and talc. The mixture was blended for five minutes and the tablets were then compressed to a weight of 1020 mg and a hardness of 14 to 16 kilograms using an elliptical punch.

It is apparent that with the teachings of this invention apply to a variety of other drugs having malflavors.

What is claimed is:

1. In combination, a particulate unpleasant flavored drug and at least 3% by weight of the combination of $SiO_2$ adsorbed on said drug particle, $SiO_2$ being present at a level sufficient to minimize the unpleasant flavor effects of the drug.

2. The combination of claim 1 wherein the $SiO_2$ is present at a level of not more than 30%.

3. The combination of claim 1 wherein $SiO_2$ is present at a level of 4–15%.

4. The combination of claims 1, 2 or 3 wherein the drug is present at a level of 30 to 70% by weight of the combination.

5. The combination of claim 1 wherein an adjunct is added to further dry the formulation.

6. The combination of claim 5 wherein the adjunct is microcrystalline cellulose.

7. A tablet formed from the combination of claim 1, 2, 3, 5 or 6 comprising at least one member selected from the group consisting of excipients, disintegrants and glidants.

8. 3-phenoxypyridine monosulfate in combination with $SiO_2$ at a level of between 3 and 20% by weight of the combination.

9. Pramiracetam in combination with $SiO_2$ at a level of between about 3 and 20% by weight of the combination.

10. Gemfibrozil in combination with $SiO_2$ at a level between about 3 and 20% by weight of the combination.

11. The combination of claims 8, 9, or 10 wherein microcrystalline cellulose is present at a level of about 5–45% by weight of the combination.

* * * * *